US010691121B2

(12) United States Patent
Stephens, Jr.

(10) Patent No.: US 10,691,121 B2
(45) Date of Patent: Jun. 23, 2020

(54) BIOLOGICALLY CONTROLLED PROXY ROBOT

(71) Applicant: Kenneth Dean Stephens, Jr., Saint George, UT (US)

(72) Inventor: Kenneth Dean Stephens, Jr., Saint George, UT (US)

( * ) Notice: Subject to any disclaimer, the term of this patent is extended or adjusted under 35 U.S.C. 154(b) by 381 days.

(21) Appl. No.: 15/822,184

(22) Filed: Nov. 26, 2017

(65) Prior Publication Data
US 2018/0217586 A1 Aug. 2, 2018

Related U.S. Application Data

(60) Provisional application No. 62/451,846, filed on Jan. 30, 2017.

(51) Int. Cl.
*G05D 1/00* (2006.01)
*B25J 13/00* (2006.01)
(Continued)

(52) U.S. Cl.
CPC ....... *G05D 1/0038* (2013.01); *A61B 5/04001* (2013.01); *A61B 5/04012* (2013.01); *A61B 5/0478* (2013.01); *A61B 5/0492* (2013.01); *A61B 5/7264* (2013.01); *B25J 3/04* (2013.01); *B25J 13/00* (2013.01); *B25J 13/087* (2013.01); *G05D 1/005* (2013.01); *A61B 2562/0209* (2013.01); *G05D 2201/0217* (2013.01); *G05D 2201/0218* (2013.01)

(58) Field of Classification Search
CPC ............... B25J 3/04; G05D 2201/0217; G05D 2201/0218; A61B 5/04001; A61B 5/04004; A61B 5/04012; A61B 5/0402; A61B 5/04025; A61B 5/0488; A61B 5/04888; A61B 5/7264; A61F 2/72; G06F 3/015
See application file for complete search history.

(56) References Cited

U.S. PATENT DOCUMENTS

| 5,481,257 A * | 1/1996 | Brubaker ............... H04N 7/185 340/12.55 |
| 2006/0195042 A1* | 8/2006 | Flaherty .................... A61F 2/50 600/544 |
| 2017/0025026 A1* | 1/2017 | Ortiz Catalan ......... G06F 3/017 |

OTHER PUBLICATIONS

Rossini et al., "Brain Machine Interfaces for Space Applications: Enhancing Astronaut Capabilities," 2009, Elsevier, vol. 86, pp. 202-204 and 207-210 (Year: 2009).*

* cited by examiner

*Primary Examiner* — Spencer D Patton

(57) ABSTRACT

Methods and systems for controlling the movements of a proxy robot utilizing electrical signals from the nervous system of a user are presented; including identifying signal pickup points on the body of the user; connecting electrodes to the pickup points; amplifying and processing the signals from each pickup point; aggregating and encoding the processed signals for transmission to a proxy robot; receiving and decoding the processed electrical signals at the location of the proxy robot into their original component electrical signals corresponding to an electrical signal from a particular pickup point on the body of the user; processing each component electrical signal by a driver configured for an individual motion-producing element in the proxy robot; addressing by the component electrical signals each motion-producing element in the motor system of the proxy robot surrogate; and causing the proxy robot surrogate to emulate every movement of the user.

20 Claims, 11 Drawing Sheets

(51) Int. Cl.
*A61B 5/04* (2006.01)
*B25J 13/08* (2006.01)
*A61B 5/0492* (2006.01)
*A61B 5/0478* (2006.01)
*A61B 5/00* (2006.01)
*B25J 3/04* (2006.01)

Biologically Controlled Proxy Robot
FIG. 1: Prior Art
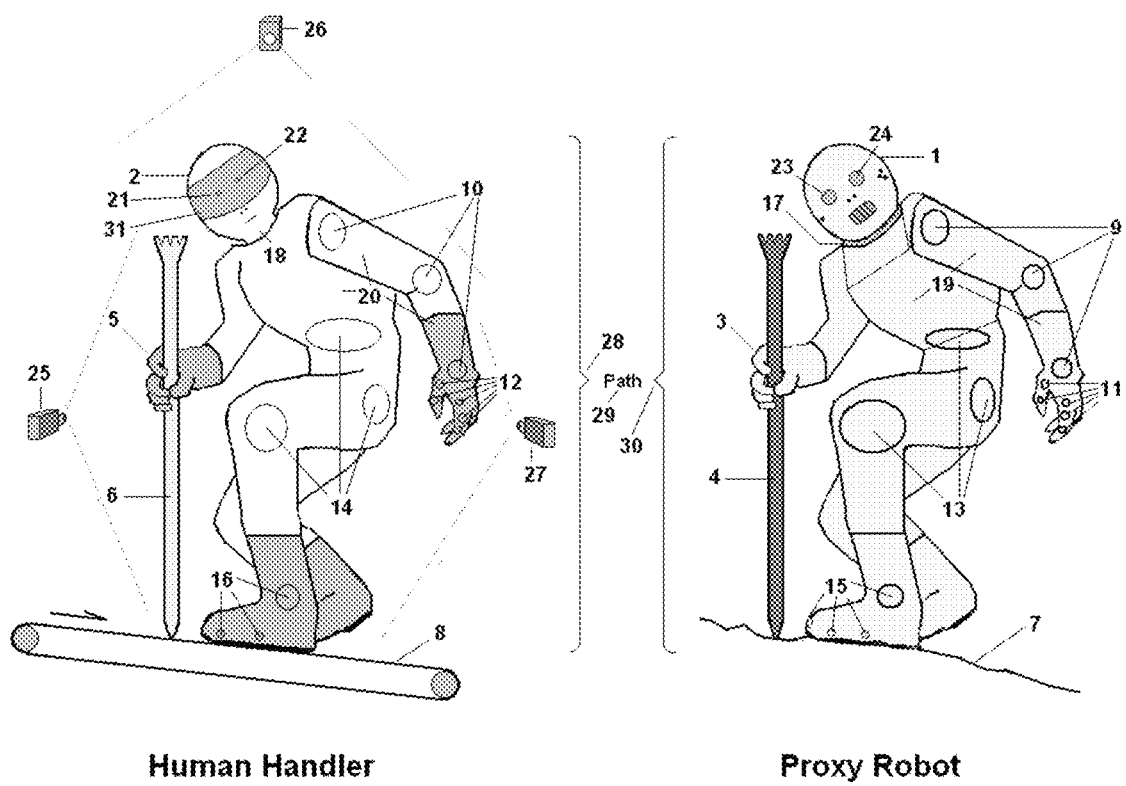
Human Handler
Proxy Robot

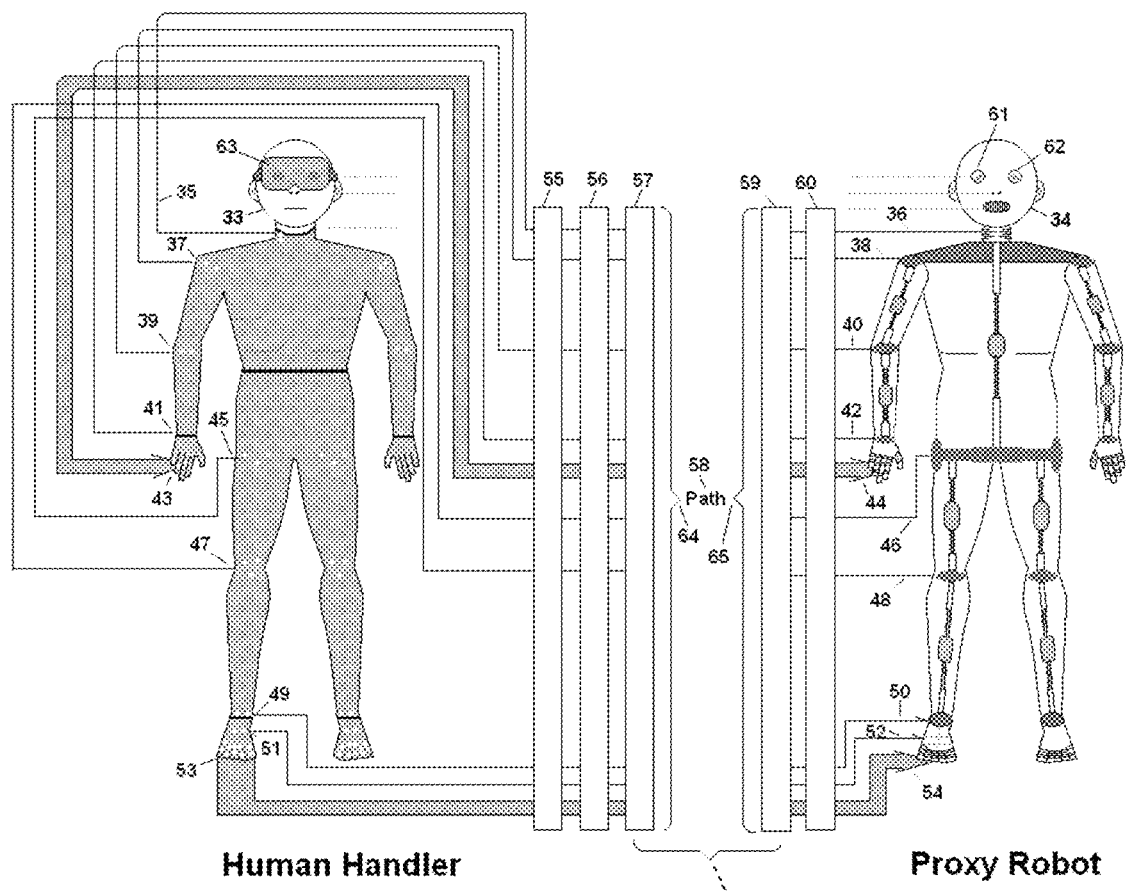
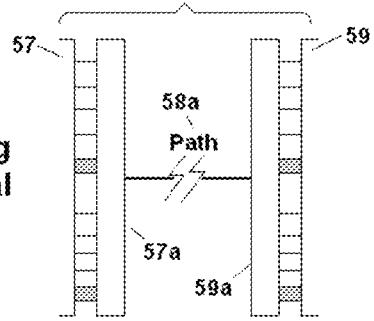

Biologically Controlled Proxy Robot

Amputee Handler with Myoelectric/Neuroelectric
Proxy Robot Controlling Means

Human Handler      Proxy Robot

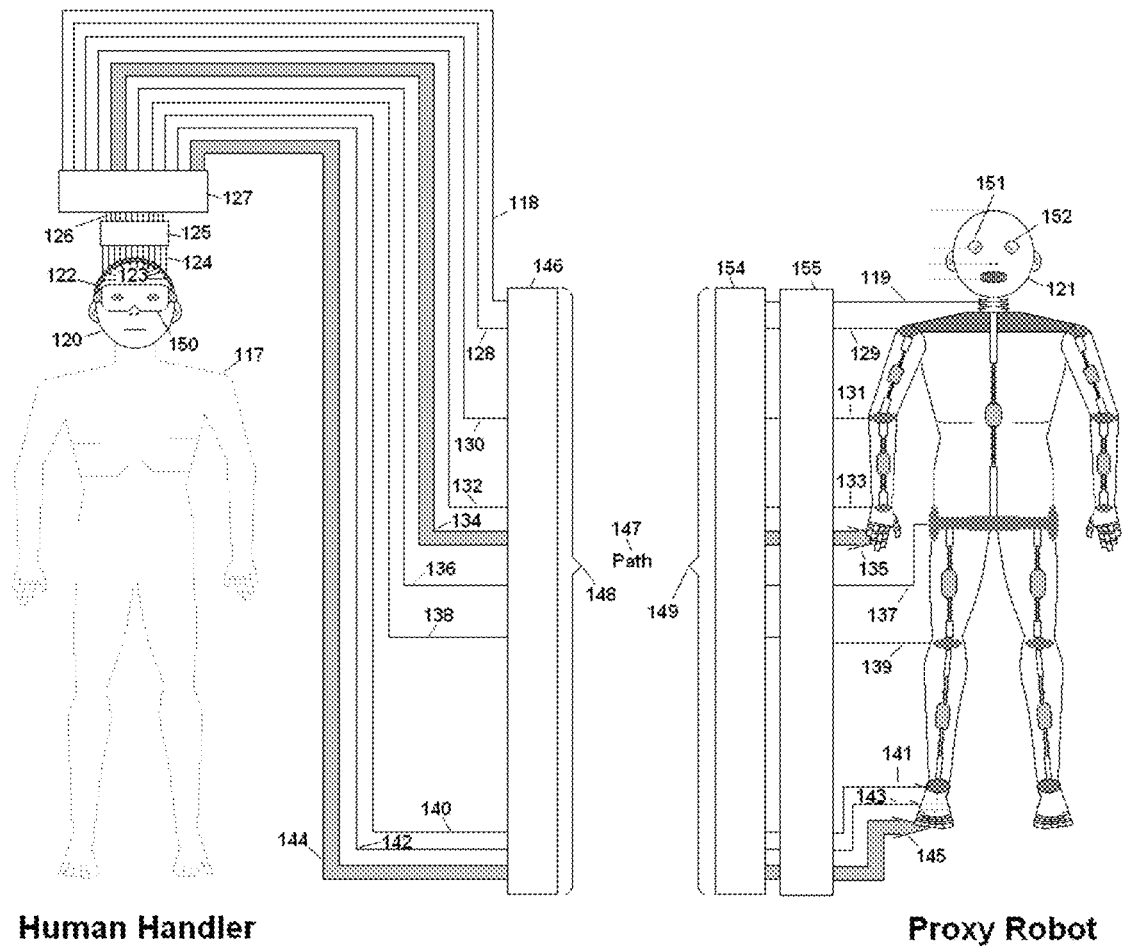

Biologically Controlled Proxy Robot

Proxy Robot Controlled by Patterns in Brain Waves and Other Electrical Signals from Body of Handler

Biologically Controlled Proxy Robot

FIG. 5: Biocontrol Training Simulators

Biologically Controlled Proxy Robot
Figure 6: Means to Control Local or Distant Proxy Robot with Brain Waves and Patterns
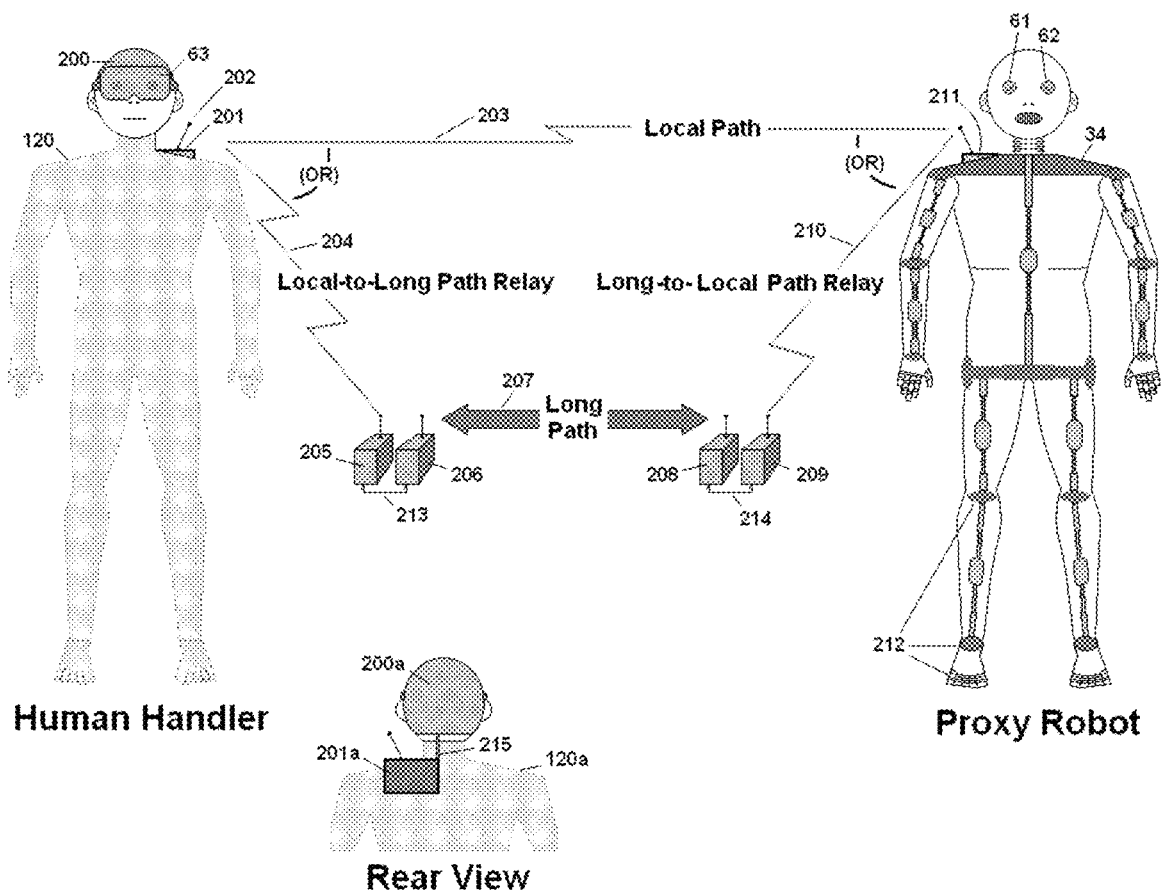
Human Handler
Rear View
Proxy Robot

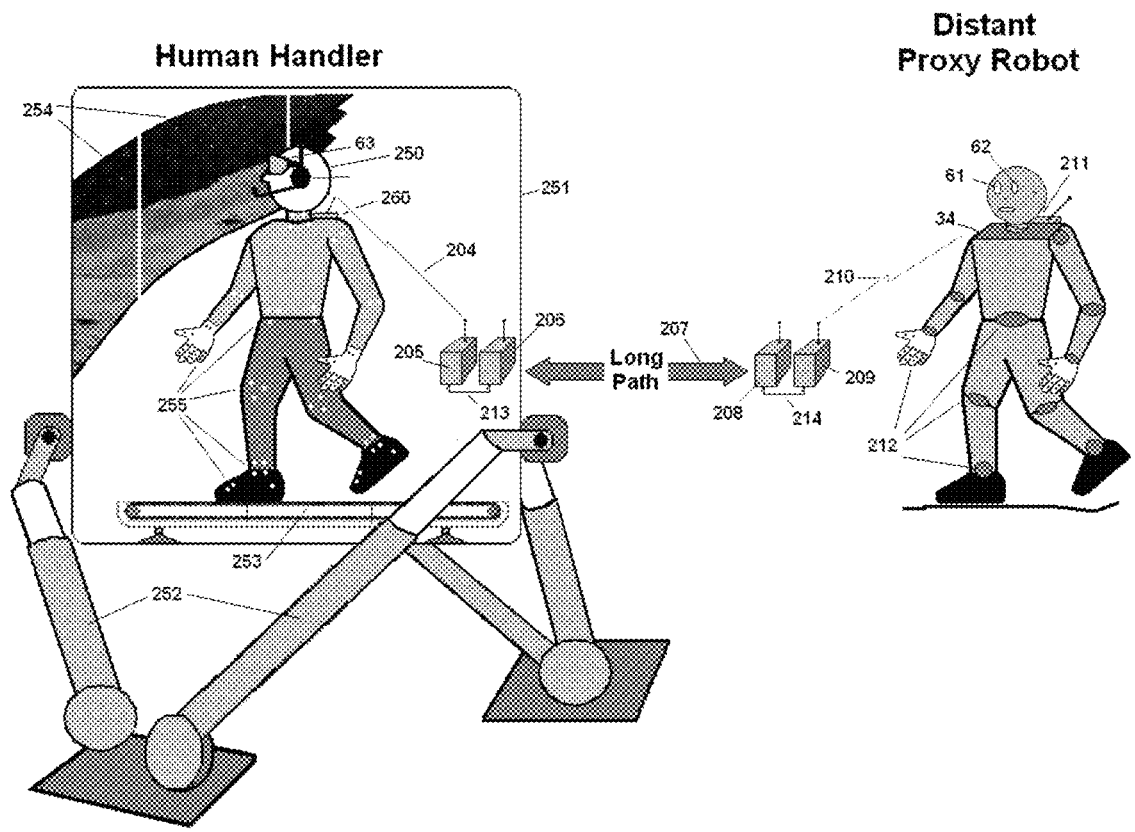

Biologically Controlled Proxy Robot

Biocontrol of Proxy Robot on Distant Planet Like Mars

Biologically Controlled Proxy Robot

Means Enabling Disabled Human Handler
to Guide Own Care Via Proxy Robot

Proxy Robot

Disabled Human Handler

Biologically Controlled Proxy Robot
Figure 10: Human Handler Controls Proxy Robot with Brain Waves, Myoelectric and Neuroelectric Signals
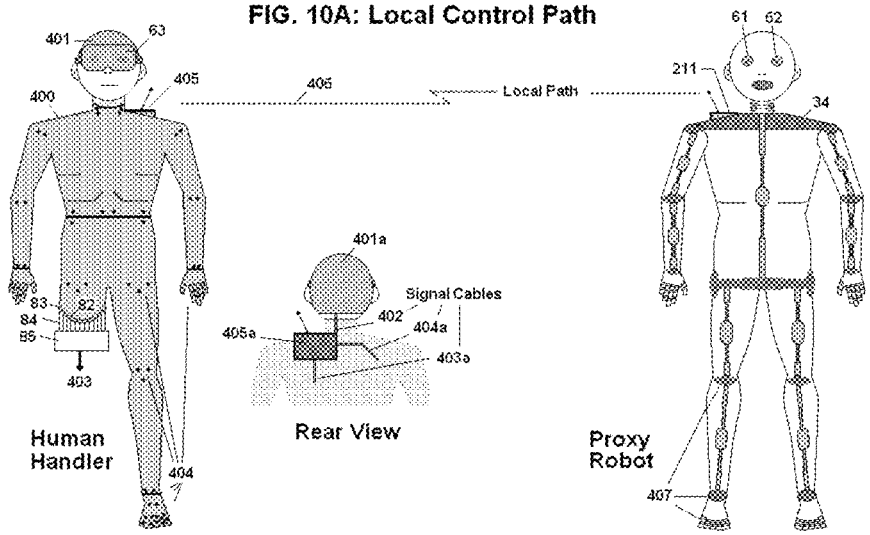
FIG. 10A: Local Control Path
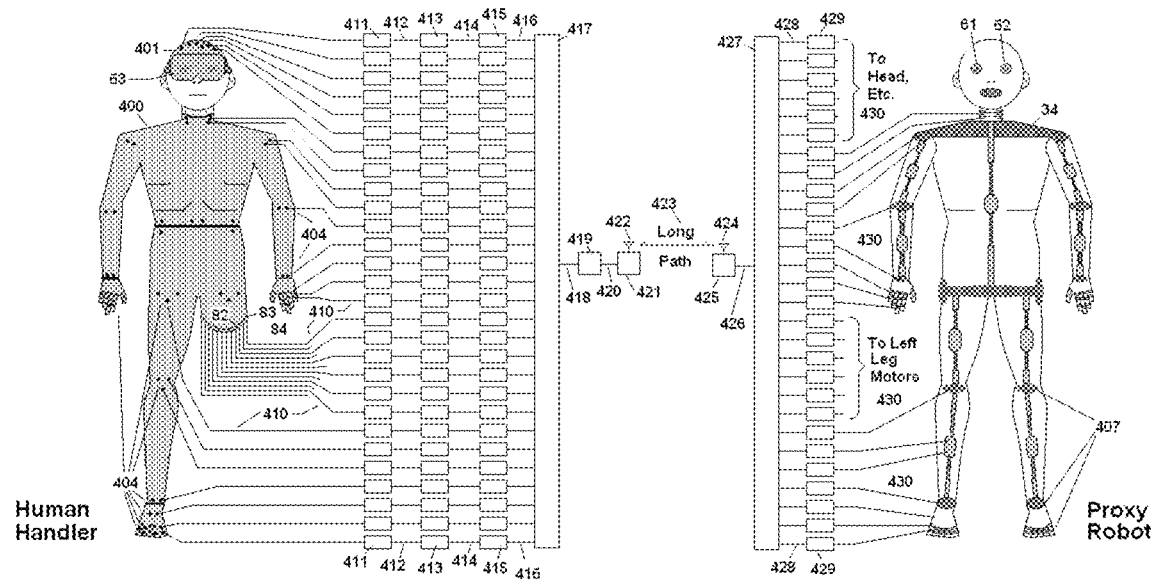
FIG. 10B: Handler on Earth, Proxy Robot in Space

BIOLOGICALLY CONTROLLED PROXY ROBOT

CLAIM OF PRIORITY

The present invention claims priority to provisional U.S. Application No. 62/451,846 filed on Jan. 30, 2017, entitled "Biologically Controlled Proxy Robot."

FIELD OF THE INVENTION

The present claimed invention generally relates to the control of a proxy robot by a human remote from that robot. More specifically the present invention relates to methods and apparatus by which humans can be enabled to control proxy robots by biological ("biocontrol") means.

BACKGROUND OF THE INVENTION

This specification is about proxy robotics and the biocontrol of proxy robots by human handlers remote from such robots. In 2009, the science fiction motion picture "Surrogates" brought proxy robotics to popular culture, with surrogate humanoid robots controlled by their human operators through unspecified "neuro-implant" connections.

In real-world prior art, a number of patents exist in the field of biocontrol, most generally with reference to the control of prosthetic limbs. For example, in "Control System for Prosthetic Devices" (U.S. Pat. No. 5,480,454 A), Bozemam Jr. teaches a system including "a transducer for receiving movement from a body part for generating a sensing signal associated with that movement," while Humphery discloses "Systems, Methods, and Devices for Controlling External Devices by Signals Derived Directly from the Nervous System" in U.S. Pat. No. 6,171,239 B1.

Similarly, in U.S. Pat. No. 7,613,509 B2, Wolf, et al teach "Systems, Methods and Computer Program Products for Transmitting Neural Signal Information," and Moll discloses a "system for controlling a computer by thoughts in the user's brain" in U.S. Pat. No. 8,350,804 B1: "Thought Controlled System."

OBJECTS OF THE INVENTION

One object of the present invention is to describe methods and apparatus enabling a human handler to control the movements of a proxy robot surrogate through various biologic means.

A second object of the present invention is to provide methods and apparatus enabling a human handler to control the movements of a proxy robot surrogate through myoelectric means.

A third object of the present invention is to provide methods and apparatus enabling a human handler to control the movements of a proxy robot surrogate through neuroelectric means.

A fourth object of this invention is to provide methods and apparatus enabling a human handler to control the movements of a proxy robot surrogate through a combination of myoelectric and neuroelectric means.

A fifth object of this invention is to provide methods and apparatus enabling a physically disabled human handler to control the movements of a proxy robot surrogate through myoelectric means.

A sixth object of the present invention is to provide methods and apparatus enabling a physically disabled human handler to control the movements of a proxy robot surrogate through neuroelectric means.

A seventh object of the present invention is to provide methods and apparatus enabling a physically disabled human handler to control the movements of a proxy robot surrogate through a combination of myoelectric and neuroelectric means.

An eighth object of this invention is to provide methods and apparatus enabling a human handler to control the movements of a proxy robot surrogate by signals from the handler's brain.

A ninth object of this invention is to provide methods and apparatus enabling a human handler to control the movements of a proxy robot surrogate by the human handler's brain wave patterns.

A tenth object of this invention is to provide methods and apparatus enabling a human handler to control the movements of a proxy robot surrogate by both signals from the human handler's brain and the same handler's brain wave patterns.

An eleventh object of the present invention is to provide methods and apparatus enabling a physically disabled human handler to control the movements of a proxy robot surrogate by signals from the human handler's brain.

A twelfth object of the present invention is to provide methods and apparatus enabling a physically disabled human handler to control the movements of a proxy robot surrogate by the human handler's brain wave patterns.

A thirteenth object of the present invention is to provide methods and apparatus enabling a physically disabled human handler to control the movements of a proxy robot surrogate by both signals from the human handler's brain and the same handler's brain wave patterns.

A fourteenth object of the present invention is to provide methods and apparatus to train both physically disabled and non-disabled human handlers to control the movements of a virutal proxy robot surrogate through the various biocontrol means described in objects 1-13.

A fifteenth object of the present invention is to provide methods and apparatus to train both physically disabled and non-disabled human handlers to control the movements of a trainer proxy robot surrogate through the various biocontrol means described in objects 1-13.

SUMMARY OF THE INVENTION

The invention disclosed herein pertains to proxy robotics and the control of proxy robots by human handlers enabled through various biocontrol methods and means.

DESCRIPTION OF THE DRAWINGS

FIG. 1 is an illustration of a human handler and proxy robot from prior art;

FIG. 2 is an exemplary illustration of a human handler and proxy robot in accordance with embodiments of the invention;

FIG. 2A depicts the addition of a parallel/serial converter to FIG. 2;

FIG. 4 is an exemplary illustration of a proxy robot controlled by human brain waves in accordance with embodiments of the invention;

FIG. 5 illustrates a number of biocontrol training simulators in accordance with embodiments of the invention;

FIG. 6 is an exemplary illustration depicting control of a proxy robot with human brain waves and patterns;

FIG. 7 is an exemplary illustration of a human handler in a body suit configured to control the movements of a distant proxy robot in accordance with embodiments of the invention;

FIG. 10 shows exemplary illustrations of means permitting a human handler to control a proxy robot with brain waves, myoelectric and neuroelectric signals in accordance with embodiments of the invention;

FIG. 10A illustrates human handler control of a proxy robot over a local path; and FIG. 10B is an exemplary block diagram illustrating human handler control of a proxy robot over a long path.

DESCRIPTION OF THE INVENTION: PRIOR ART

Figure 3:
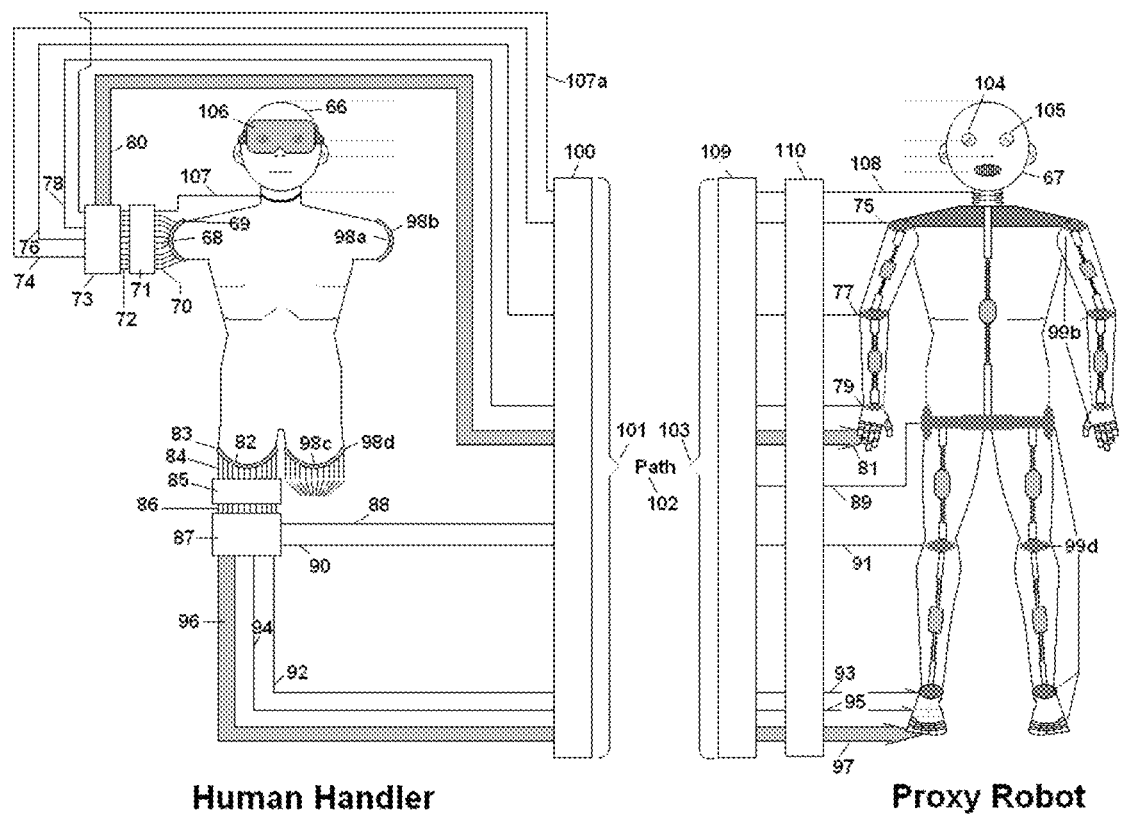
FIG. 3 is an exemplary illustration of an amputee user connected to a proxy robot in accordance with embodiments of the invention.

Current humanoid robots generally have a head, limbs, joints, hands and feet corresponding to those of a human. Humanoid robots are bipedal, moving about on two feet and staying balanced via software hard-coded into their motor systems or originating externally. Operating code may consist of prerecorded software algorithms or originate from a person at a keyboard, joystick or a graphical user interface (GUI). For example, the "Nao" robot produced by Aldebaran Robotics in France https://en.wikipedia.org/wiki/Nao (robot), can be programmed with C++, Python, Java, MATLAB, Urbi, C, and Net, and also runs on Windows, Mac OS and Linux GUIs. In one embodiment of the present invention, electrical signals are read from pickup points on the body of a human handler going through various motions, and patterns in the signals representing specific body movements are identified and converted to operating code to produce the same movements in a proxy robot.

FIG. 1 illustrates a prior art configuration of a proxy robot surrogate 1 and its human handler 2, generally following FIG. 2A in the inventor's copending U.S. patent application Ser. No. 15/384,321. Note that the body position of both handler and proxy robot is the same, with the proxy following all the handler's moves. For example, in the handler's right hand 5 is a bar tool 6 for breaking and prying rocks. Proxy robot 1 is also holding a bar tool 4 in its right hand 3. Note as well that the robot is being made to walk up a slight hill 7, the incline of which is duplicated by mechanisms controlling a treadmill 8, under the human handler which may be a manual treadmill controlled by the human handler's feet. Alternatively, the controlling mechanism is a motorized treadmill that automatically re-centers the handler after each step. Such control of handler pitch, roll and heading is covered in various embodiments in inventor's U.S. patent application Ser. Nos. 15/384,321 and 14/271,437, now U.S. Pat. No. 9,821,465. Pitch and other positional aspects of handler's treadmill 8 are continually adjusted in the handler environment from computer-driven mechanisms analyzing video and other signals from the proxy robot.

Follow-me data 28 flows continually from human handler to proxy robot. For example, joints 10 in the arm and wrist of human handler 2 continually send positional and joint angle data to the robot for follow-me replication 9 by the proxy. Similar data is sent from hand and finger joints 12 in the human handler for replication in the same joints or hinges 11 in the robot. Torso and leg angles in the human 14 are also sent as data to the proxy for replication 13, and joint angles in the feet of the handler 16 are translated into data for replication 15 in the proxy robot.

There are a number of means by which joint angle and similar data can be monitored and sent. One possibility is via clothing with built-in strain gauges at critical joints; another is from similar strain gauges in special elastic bands fitted for wear on the knees, ankles, elbows and so forth. Gloves, stockings and booties can also contain strain gauges. Another approach involves gyroscopic position marking, especially of the head's various angles. While only one side of human and proxy are depicted, is to be appreciated that similar data emanates from the right arm and leg of the human to control those sections of the proxy as well.

Depending on the need of the mission and complexity of the proxy robot, data may be sent from many more points on the human for replication by the proxy. Vital sensors would continuously monitor the side-to-side angle (yaw or heading), up-down angle (pitch), and sideways tilt (roll) of the human's head, labeled at point 18 in the drawing. All of these angles would be faithfully replicated by the proxy robot, as labelled at point 17. This latter interchange of data is extremely important, since it duplicates the human acts of scanning, analyzing and "looking around."

Another method of sending follow-me movement and positional data from handler to proxy is discussed in Inventor's U.S. patent application Ser. No. 15/384,321; namely, the use of motion capture technology to monitor the same critical joint and movement areas by camera or other means. Depicted in the drawings are three representative motion capture cameras 25-27 spaced around the handler to capture the handler's every move. Data from these cameras is sent to a computer for analysis which is translated to near-real time movement commands to the proxy robot.

There are approximately 230 joints in the human body, but as few as 50-60 points of movement can often suffice for robots and their human handlers. Wherever the robot is stiff and inflexible, the human will feel the same inflexibility in this exemplary embodiment, as noted by rigid areas 19 on the arm and torso of the proxy and the same areas 20 on the handler.

A head mounted display 31 receives 3-D video information as part of a data bundle 30 from the right and left eye cameras 23, 24 of the proxy robot for viewing and processing by the human handler's right and left eyes 21, 22. Thus it can be seen that the data travelling over path 29 between human handler and proxy robot is a two-way channel which includes not only the follow-me data 28 aggregated from various points of movement on the handler and flowing to the proxy, but also critical information 30 flowing from proxy robot to human handler, including visual data from the robot's eye cameras. Throughout the present application, this data exchange path 29 might be as short as a small cable or wireless link between a human handler and proxy robot in close proximity or as long as the distance to a far-off destination in space.

DESCRIPTION OF THE DRAWINGS: CURRENT INVENTION

FIGS. 2 to 5 illustrate methods and apparatus for controlling the movements of a proxy robot through biocontrol means as taught in the present application. In FIG. 2, a user (human handler) 33 can control the movements of a proxy robot surrogate 34 through myoelectric means, neuroelectric means or some combination of myolectric and neuroelectric means. Myoelectric signals, also known as EMG or electromyography signals, are changes in electrical potential in muscle cells when these cells are electrically or neurologically activated, as by human movement or attempted movement; neuroelectric signals are small electrical signals generated by the nervous system, and both types of signal pass through the central nervous system (the brain). While myoelectric signals are generally found in the body's motor system and neuroelectric signals are generally sensory in nature, the latter signals often trigger motor response.

In the drawing, a plurality of optimally-placed electrodes pick up myoelectric or neuroelectric signals from scanning a human handler's body for optimal sensory or movement electrical signal pickup points. For example, muscles or nerves in the neck produce small signals 35 representing movement or position of the head, signals which are amplified in a signal amplifier 55, then processed by a signal processor 56 and then passed to an encoder 57. It should be noted that both signal amplifier 55 and processor 56 blocks represent a multiplicity of individual amplifiers and processors, each concerned with a myoelectric or neuroelectric signal picked up from the body of handler 36. It is also to be appreciated that while only signals from the right sides of the handler and proxy robot are depicted in FIGS. 2-5, a set of signals from the handler's left side are similarly sent to mechanisms controlling the left side of the proxy robot. Moreover, while only a dozen or so myoelectric/neuroelectric pickup points are depicted in FIGS. 2-5, the actual number of pickup points and resulting signal paths may be greater or lesser in practice, depending on such factors as desired mobility, movement range and motion smoothness in the proxy robot.

In FIG. 2, myoelectric and/or neuroelectric signals 35 from the neck of the human handler and representative of neck and head movement are amplified by a signal amplifier 55, at or near the point of skin contact to maintain the best signal-to-noise ratio, to a level allowing analog-to-digital conversion and processing by signal processor 56 before entering a signal encoder 57 which aggregates processed signals 64 from points all over the human handler's body, converts this parallel information into a serial data stream, and sends the serial stream over a path 58 which may represent anything from a very short cable or wireless link in a room to a transmission path of millions of miles to Mars or some other point in distant space.

Similarly, myoelectric and/or neuroelectric signals are picked up from points on the human handler representative of shoulder and upper arm movement 37, elbow and lower arm movement 39, wrist and hand movement 41, finger movement 43 (wide channel denotes multiple connections to individual fingers), hip and upper leg movement 45, knee and lower leg movement 47, ankle movement 49, foot movement 51, and toe movement 53, where the depicted wide channel represents multiple connections to individual toes.

While the myoelectric or neuroelectric signal from each of these pickup points is individually amplified by a signal amplifier generically labelled 55 in the drawing, it is to be appreciated that the exact nature of each signal will require custom amplification by its corresponding signal amplifier to prepare it to be converted from analog to digital and processed by an individual section of analog-to-digital (A/D) converter and signal processor 56. All of the resulting signals from processor 56 are fed into encoder 57 for aggregation and streaming over path 58.

FIG. 2A depicts the conversion of the aggregated signals from encoder 57 from parallel signals to serial by parallel/serial converter 57a for transmission over path 58a as a serially-encoded, streaming signal train to serial/parallel converter 59a on the robot side of path 58a which reconverts the handler movement signals into parallel signals for decoder 59 to send as follow-me signals to robot motion drivers 60 in the proxy robot. In environments where the proxy robot is local to the human user (handler), amplified electrical signals from pickup points on the handler may be sent in analog form over a multi-wire cable or similar parallel means directly to the proxy robot. In this case, neither parallel/serial converter 57a nor serial/parallel converter 59a on the robot side of path 58a will be needed.

In FIG. 2 and other drawings in this specification, only biological signals from the right side of the human handler are shown. This depiction is for clarity only, and it is to be understood that similar pickup points, signal amplifiers and processors from the left side of the handler also enter encoder 57 for transmission over path 58, where they are received by a decoder 59 which separates signals into their component parts for appropriate amplification and processing by robot motion drivers 60 which output analog or digital signals to a number of motion-producing means on the proxy robot corresponding to each pickup point on the human handler. Typical motion-producing means include motors, solenoids, springs, elastic materials, artificial muscle means, hydraulic systems, pneumatics, transducers and other devices.

Thus it can be seen that movement signals 35 from the neck and head of the human handler 33 are ultimately translated by decoder 59 and motion driver 60 into signals 36 which produce corresponding movement in the neck and head of the proxy robot 34. Similarly, signals from other points 37, 39, 41, 43, 45, 47, 49, 51 and 53 on the human handler are processed, transmitted, received and re-processed to feed corresponding motion-producing means on the proxy robot at points 38, 40, 42, 44, 46, 48, 50, 52 and 54, with the same thing happening on the left side of both handler 33 and proxy 34. In this manner, movements made by the human handler can be faithfully reproduced by the proxy robot.

Path 58 is, of course, two-way in nature. While follow-me signals 64 travel from human handler to proxy robot, various feedback signals 65 are sent in the reverse direction from robot to human. Chief among the feedback signals are video signals from the robot's stereoscopic (3-D) eye cameras 61, 63 which are received in a display means at the human handler side. Such display may take the form of a 3-D head-mounted display 63 as depicted, or may be in the form of a screen or panel or some combination of these. In any case, this visual information from the proxy robot's eye cameras enables the human handler to see what the robot is seeing; to cause the robot to "look around" when the handler turns his/her own head; and to thereby guide the proxy robot through the parameters of any particular situation.

Other signals which originate at the proxy robot and travel back to the human handler may include ambient sounds (from one or more microphones on the robot), smells (from suitable pickup means on the robot), and even tastes. "Smells and tastes" may also include analysis of gasses, chemicals and the makeup of soils, rocks and so forth. Haptic pickup means such as touch and heft (weight) may also be employed in the robot, and would move over path 58 in a direction 65 from proxy robot to human handler.

FIG. 3 illustrates a special case. On the proxy robot 67 end of things, this drawing is largely identical to FIG. 2 above, but the human handler 66 depicted in this figure has stumps 68, 98a in place of right and left arms and stumps 82, 98c in place of right and left legs. While this illustrates an extreme case of either a person with quad amputation or born without limbs, a more typical situation might be some combination of the human handlers shown in FIGS. 2 and 3. For example, the handler may have a single missing arm, two missing legs, or so forth, in which case points on the non-missing limbs would bio-couple to their respective signal amplifiers and connections in accordance with the description of FIG. 2.

This discussion will concern itself with the right side of the human handler, with left stumps 98a, 98c and pickup interfaces 98b, 98d to be connected in similar fashion. Upon right arm stump 68 is placed an interface device 69 which is made to maintain an exact position on that stump in such wise that a number of individual contact points 70, each corresponding to the pickup points for myoelectric or neuroelectric signals pertaining to the movement of the handler's shoulder, upper arm, elbow, lower arm, wrist, hand and fingers may be detected and conveyed to individual sections of a signal amplifier 71 which is preferably mounted in close proximity to interface 69. The purpose of signal amplifier 71 is to bring all signals from stump 68 and interface 69 to levels appropriate for A/D conversion and processing in individual sections of processor 73 corresponding to each signal.

In like manner, upon the human handler's right leg stump 82 is placed or mounted an interface device 83 which is made to maintain an exact position on the right leg stump in such wise that a number of individual contact points 84, each corresponding to the pickup points for myoelectric or neuroelectric signals pertaining to the movement of the handler's right hip, upper right leg, knee, lower leg, ankle, foot and toes may be detected and conveyed to individual sections of a signal amplifier 85 which is preferably mounted in close proximity to interface 83. As in the case of the discussion above with reference to the handler's right arm stump, the purpose of signal amplifier 85 is to bring all signals from right leg stump 82 and interface 83 to levels appropriate for A/D conversion and processing by sections of processor 87 corresponding to each signal.

The signal pickup locations on interface devices 69, 83, 98b and 98d may be on the surface of the skin of each stump; may be subdermal in nature; or may represent devices implanted in the stump, including probes, microchips and a variety of connection mechanisms.

The digitized and processed signals from both right arm stump processor 73 and right leg stump processor 87 are directed, along with similar signals from the handler's left arm stump and left leg stump, into an encoder 100. Signals from the right arm stump include those needed to move the right shoulder and upper arm 74, right elbow and lower arm 76, right wrist and hand 78, and right fingers 80, while signals from the right leg stump include those needed to move the right hip and upper leg 88, knee and lower leg 90, ankle 92, foot 94 and toes 96. Signals from sensor 107 on the human handler's neck would similarly be amplified 71, sent to A/D converter and processor 73 and routed 107a to encoder 100. It is to be understood that encoder 100 would also have sections pertaining to signals from the handler's left arm stump and left leg stump.

While the myoelectric or neuroelectric signal from each of the pickup points on the human handler's stumps is individually amplified by a signal amplifier generically labelled 71 and 85 in the drawing, it is to be appreciated that the exact nature of each signal will require custom amplification by its corresponding signal amplifier segment to prepare it to be converted from analog to digital and processed by an individual section of A/D converter and signal processors 73 and 87. All of the resulting signals from these processors are fed into encoder 100 for aggregation and streaming over path 102.

Thus, encoder 100 aggregates processed signals from points all over the human handler's body 66 and sends them over a path 102 which may represent anything from a very short cable or wireless link in a room to a transmission path of millions of miles to Mars or some other point in distant space. At the far (proxy robot) end of this path, a decoder 109 decodes the various body-part motion signals and routes each to the appropriate section of a group of robotic motion drivers 110.

So it can be seen that movement signals 107 from the neck and head of the human handler 66 are ultimately translated by decoder 109 and motion driver 110 into signals 108 which produce corresponding movement in the neck and head of the proxy robot 67. Similarly, signals from other points 74, 76, 78, 80, 88, 90, 92, 94 and 96 on the human handler are processed, transmitted, received and re-processed to feed corresponding motion-producing means on the proxy robot at points 75, 77, 79, 81, 89, 91, 93, 95 and 97, with the same thing happening on the left side of both handler 66 and proxy 67. In this manner, movements made in the brain, nervous and muscular system of human handler 66 can be translated into actual robotic movements by the decoder 109 and robotic motion driver bank 110 in proxy robot 67.

Here again, path 102 is two-way in nature. While follow-me signals 101 travel from human handler to proxy robot, various feedback signals 103 are sent in the reverse direction from robot to human. Chief among the feedback signals are video signals from the robot's 3-D eye cameras 104, 105 which are received by a display means 106 at the human handler side. Such display make take the form of a 3-D head-mounted display 106 as depicted, or may be in the form of a screen or panel or some combination of these. In any case, this visual information from the proxy robot's eye cameras enables the human handler to see what the robot is seeing; to "look around" by turning her head; and to thereby guide the proxy robot through the parameters of any particular mission.

Other signals which may originate at the proxy robot and travel back to the human handler may include ambient sounds (from one or more microphones on the robot), smells (from suitable pickup means on the robot), and even tastes. "Smells and tastes" may also include analysis of gasses, chemicals, etc. as described under FIG. 2. Haptic pickup means such as touch and heft (weight) may also be employed in the robot, and would move over the path 102 in a direction 103 from proxy robot to human handler.

The human handler 66 illustrated in FIG. 3 has one or more physical limitations or disabilities, as represented as having stumps rather than right and left arms and stumps in place of right and left legs. This extreme case may be the result of amputations (as, for example, from serious battle injuries) or may also be caused by birth defects resulting in all or some of the missing limbs. A more typical example might be an individual missing a single arm or leg, or some portion thereof. In such a case, biocontrol signals might be read from the "normal" portions of the individual in the manner shown in FIG. 2, and from "stump" portions in the manner of FIG. 3.

In whichever case, the invention could serve to positively impact the quality of life of an individual with one or more missing limbs in several distinct ways:

1) The utilization of physically disabled persons as proxy robot handlers could well provide them with vocational opportunities, with them and their proxy robots employed in construction, teaching, medicine and at many other jobs a non-proxy robot human might do.
2) A physically disabled person might be employed as a professional proxy robot handler, guiding her/his robot through a host of specialized tasks.
3) The proxy robot of such a physically disabled person might also become that person's own arms, legs, hands and feet, allowing the individual in question to effectively become her/his own caregiver.

In the figure to follow, all the above-listed opportunities apply, even though the next drawing might well represent the most severe cases of physical disability imaginable.

FIG. 4 depicts a proxy robot 121 controlled by the brain waves and brain wave patterns of a human handler 120. The handler in question may have physical abilities ranging from total to near none at all. In the drawing, interface device 122 makes contact with specific signal pickup locations 123 on the head of human handler 120: locations which may include the top, sides, rear and frontal area (forehead) of the handler. The handler's body 117 below the head is shown in gray to indicate that it plays no role in the configuration illustrated in FIG. 4.

Pickup locations 123 may be on the surface of the skin of the handler's head; may be subdermal in nature; or may represent devices implanted in the skull or brain of the human handler 120, including probes, microchips and a variety of connection mechanisms. Wires 124 take the neuroelectrical signals that constitute brain waves from interface device 122 and its various pickup locations 123, conveying each of these signals to a section of a signal amplifier 125, where each signal can be amplified to a level sufficient to be processed by a brain wave interpreter 127. Signal processing may include A/D conversion; however, it may be important to have analog as well as digital versions of each signal available for analysis and processing by interpreter 127.

Brain wave interpreter 127 is a powerful microcomputer, capable of being programmed externally to respond to the brain waves and brain wave patterns of a given individual. Its primary function is to translate various brain waves and brain wave patterns into the meaningful movement of a proxy robot's component parts. For instance, one interpreter output 118 will produce movement in the robot's head and neck 119, while another output 128 corresponds to movement in the robot's right shoulder and upper arm 129. Similarly, output 130 will produce motion in the robot's right elbow and lower arm 131; output 132 is concerned with movement of the robot's right wrist and hand 133; output 134 produces movement in the robot's right fingers 135; output 136 causes movement in the robot's right hip and upper right leg 137; output 138 will direct motion in the robot's right knee and lower right leg 139; output 140 is concerned with the movement of the proxy robot's right ankle 141; output 142 directs movement of the robot's right foot 143; and output 144 produces movement of the proxy robot's right toes 145. Other outputs will direct movement on the left side of proxy robot 121.

Another task of interpreter 127 is to identify brain wave patterns—signal combinations from each user that can indicate more specific movements like the closing of a little finger—for transmission to proxy robot 121 Signal processor groups 56 in FIGS. 2; 73 and 87 in FIG. 3; and 413 in FIG. 10B can likewise share information among themselves to identify such useful signal patterns prior to transmission to a proxy robot.

The output signals from interpreter 127 are directed into an encoder 146 which aggregates all signals for transmission along a path 147 which may be a local cable or may constitute transmission to a far-off planet or similar destination. At the far (proxy robot) end of path 147, the aggregated signals enter a decoder 154 which returns them to their parallel, individual motion-producing, states. The signals from decoder 154 are further directed into a set of robot motion drivers 155, each member of which produces output voltages and currents capable of operating motion-producing mechanisms located in various parts of the proxy robot, per the paragraph above.

As in proceeding figures, path 147 is two-way in nature. While follow-me signals 148 travel from human handler to proxy robot, various feedback signals 149 are sent in the reverse direction from robot to human. Chief among the feedback signals are video signals from the robot's stereoscopic (3-D) eye cameras 151, 152 which are received in a display means 150 at the human handler side. Such display make take the form of a 3-D head-mounted display as depicted, or may be in the form of a screen or panel or some combination of these. In any case, this visual information from the proxy robots eye cameras enables the human handler to see what the robot is seeing; to "look around" by turning its head; and to thereby guide the proxy robot through the parameters of any particular mission. Other feedback may include haptic (touch, heft) signals, "smell" and "taste" (liquid and gas analysis), and so forth.

While the human handler 66 depicted in FIG. 3 may be physically disabled by lack of one or more arms and legs, the human handler 120 of FIG. 4 might present a much wider range of physical disabilities, including loss of motor control. Brain wave detection may be able to bypass such disabilities, allowing even a severely disabled person to do meaningful physical activity via her proxy robot. Moreover, since the electronics in signal amplifier 125, interpreter 127 and encoder 146 can be made extremely small and lightweight, it is entirely possible to combine these circuits with a radio or modulated light transceiver (including Bluetooth©, WiFi©, infra-red and a multiplicity of other transceiver means), wearable on the person of the human handler.

The above description leads to a scenario wherein severely disabled persons might assume control of their own lives, essentially becoming their own caregivers. For example, a physically disfunctional person could look at his own limp body through the eye cameras of his proxy robot surrogate, and actually guide that robot through such self-caregiving acts as bathing, feeding and dressing that body— his own body—as seen and handled by the proxy robot as described under FIG. 9 below.

Figure 4A:
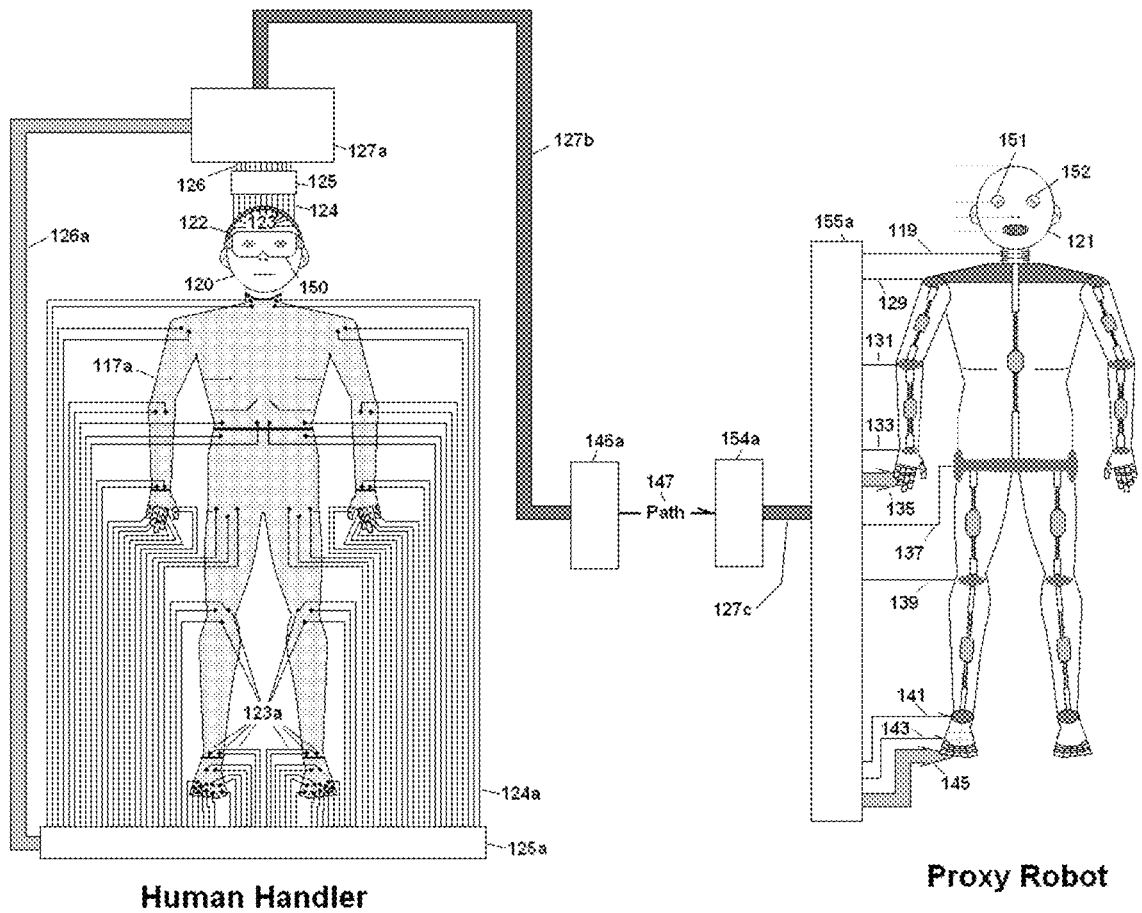
FIG. 4A is an exemplary illustration of a proxy robot controlled by patterns in signals from the brain and other points on the body of a human handler.

In FIG. 4A, the identification of patterns by a pattern interpreter need not be limited to patterns in brain waves alone, but rather in electrical signals optimally located from scanning the body of a human handler 120. In this illustration, electrodes in contact with electrical signal pickup points (c.f. 123a) corresponding to the handler's joints, muscles and nervous system are connected 124a to individual signal amplifiers placed in proximity to each pickup point, not in a single amplifier block 125a as shown for simplicity. On the head of handler 120, Interface device 122, signal pickup locations 123, connecting wires 124 and signal amplifier 125 are the same as in FIG. 4 above.

In all locations, electrode connection may include taping, contact via a body suit 117a or subdermal implantation, and each signal amplifier will provide sufficient electrical signal output 126a to be read and processed by pattern interpreting computer 127a. Computer 127a performs a number of functions:

1) Whenever a new move of a particular human handler user 120 is noted by either observational analysis by a human monitor or by automated motion capture devices, computer 127a identifies patterns in the electrical signals generated by that handler and associates the patterns with both the new move and the particular human handler.
2) Computer 127a then translates the handler move into lines of operating code which will command proxy robot 121 to initiate exactly the same move.
3) As various handlers go through a comprehensive series of moves, computer 127a assembles a lexicon of proxy robot operating code lines associated with each move of a specific handler and similar lexicons for the body signals of other human handlers, each accessible by the computer when its associated handler is being monitored.
4) In a proxy robotic mission, proxy robot 121 is placed in a mission environment remote from human handler 120 who is placed in a simulation of the remote mission environment. As handler 120 moves through the simulated environment, signals associated with each move will emanate from pickup points 123, 123a on the head and body of the handler to be amplified by signal amplifiers 125, 125a.
5) Amplified signals 126, 126a from handler 120 will continuously flow into computer 127a which monitors them for patterns indicating movement by handler 120.
6) As computer 127a identifies a move associated with a particular signal pattern by handler 120, the computer will locate the lines of proxy robot operating code associated with that move in its lexicon.
7) As soon as computer 127a locates each line of operating code, it places the code into a queue to stream 127b to proxy robot 121 at the remote mission site.
8) As human handler 120 moves around in the simulated environment at mission control, computer 127a will produce a stream 127b of digital commands representing each move of human handler 120. The digital command stream is directed to a transmitter 146a (which may also comprise a line driver if the mission site is near enough to connect by cable) for transmission over a path 147 to a receiver 154a at the mission site. The receiver separates digital command stream 127c, identical in content to digital command stream 127b but delayed by transmission over path 147, from other mission data and feeds it to proxy robot operating computer 155a which translates the streaming digital commands into motion actuator driver signals, each capable of operating a motor, hinge or other motion-producing mechanism in proxy robot 121. In this manner, a proxy robot surrogate in a distant place like a mission site on Mars can emulate every move of its human handler at mission control on Earth.

Figure 5A:
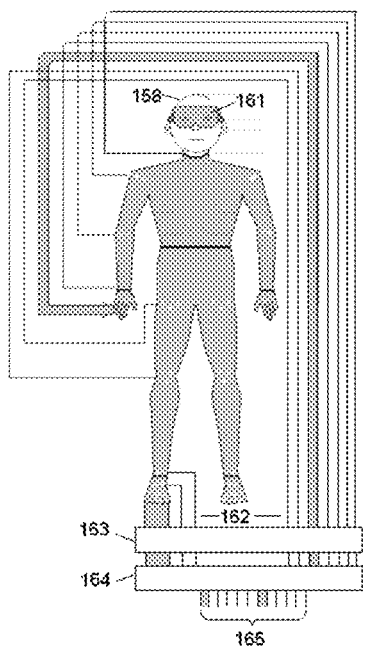
FIG. 5a illustrates a human handler connected in accordance with the embodiment in FIG. 2.
Figure 5B:
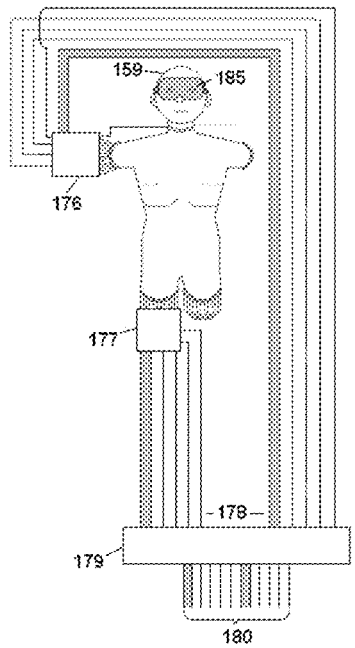
FIG. 5B illustrates a human handler connected in accordance with the embodiment in FIG. 3.
Figure 5C:
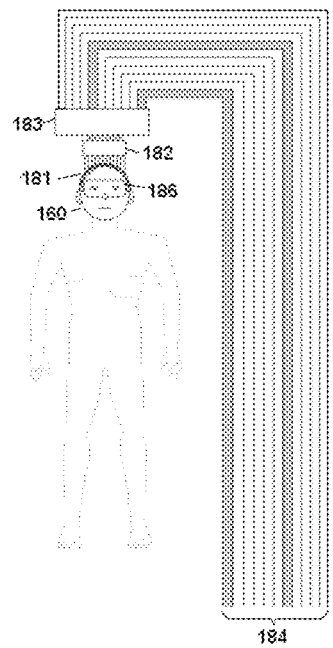
FIG. 5C illustrates a human handler connected in accordance with the embodiment in FIG. 4.

FIG. 5 illustrates training simulators for the three biocontrol scenarios shown in FIGS. 2 through 4 above, with FIGS. 5A, 5B and 5C depicting the human handler end of things; FIG. 5D representing one training scenario; and FIG. 5E representing another training scenario.

Figure 5D:
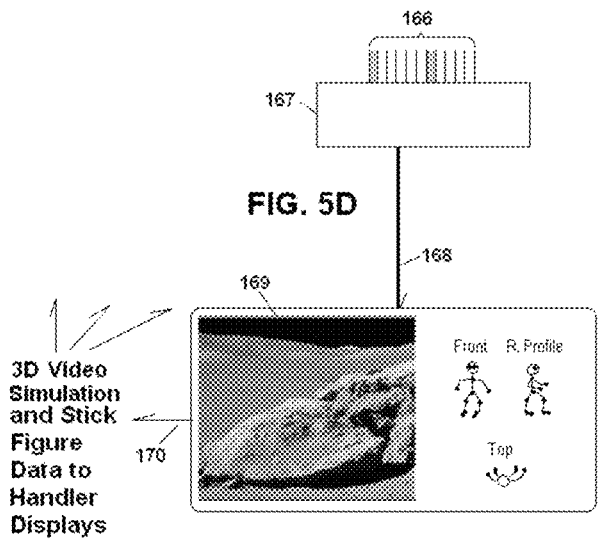
FIG. 5D illustrates connection to a video and graphics rendering computer in accordance with embodiments of the invention.

In FIG. 5A, the human handler 158 is the same as human handler 33 in FIG. 2, with signal pickups 162 in pertinent locations on the handler's body directed to a multi-section signal amplifier 163, processor and A/D converter 164 and output lines 165 which can connect in one of two ways to be described under FIGS. 5D and 5E below.

In like manner, in FIG. 5B the human handler 159 is the same as human handler 66 in FIG. 3, with stump signal pickups feeding signal amplifiers 176 and 177 and the resulting amplified signals 178 directed into processor and A/D converter 179 which produces output lines 180.

In FIG. 5C, the human handler 160 is the same as human handler 120 in FIG. 4, with signals from pickups and interface 181 entering signal amplifier 182 and brain wave/ brain wave pattern interpreter 183, the latter producing output lines 184. It can be seen that the output lines 165, 180 and 184 all produce a set of signals corresponding to movement in the same areas of a proxy robot, and thus can be used relatively interchangeably in the training simulators of FIG. 5.

There are two specific ways that the signals from these robotic motion outputs 165, 180 and 184 may be utilized to train human handlers in a simulated environment. In FIG. 5D, the output signals from any one of the three scenarios represented in FIGS. 5A-5C are directed 166 into a video and graphics rendering computer 167 which creates a virtual proxy robot operating in a virtual environment. Visual information from computer 167 is routed 168 to the video display of whichever individual 158, 159 or 160 is to undergo training as a proxy robot handler. So if the handler 158 in FIG. 5A is in training, the visual and graphic information 170 shown in screen 169 is what handler 158 will see on her/his display 161.

Included in the display information 169 is virtual video from the simulated camera "eyes" of a simulated robot (left), as well as stick or wire figures or more complete representations of the same simulated robot's position or stance at any given moment. While front, right profile and top down views are depicted in FIG. 5D, the views may be any that assist in the training of the human handler. Put in other terms, computer 167 in FIG. 5D generates a simulation of a proxy robot capable of moving through a virtual video environment. Obviously, this form of simulation can be used as well for the handler scenarios represented in FIGS. 5B and 5C.

Figure 5E:
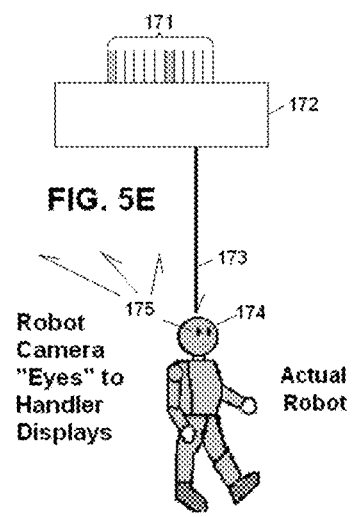
FIG. 5E illustrates connection to a proxy robot in accordance with embodiments of the invention.

In FIG. 5E, an output circuit 165, 180, 184 from any one of FIG. 5A, 5B or 5C is selectively connected 171 and directed to a set of robotic motion drivers 172 similar to those described in FIG. 2 (60); FIG. 3 (110); and FIG. 4 (155). Unlike the proxy robots in FIGS. 2-5, however, motion driver array 172 directs 173 the movements of a smaller, cheaper training robot 174. Consequently, the robotic motion-producing signals from driver array 172 are likely to be of lower voltage and/or current, or may be adapted by the driver array to digital form, constituting a program to address motion producing systems in the smaller robot 174. In this figure, the robot 174 will incorporate video eye cameras to stream live, real-time video 175 to the display of whichever human handler is undergoing training.

So, for example, a physically disabled human handler lacking one or more arms and legs such as handler 159 in FIG. 5B and with stumps connected to the circuitry previously described might be linked to a small training robot 174 by connecting output lines 180 to the input lines 171 of the robot motion driver array, allowing that handler to practice putting the training robot 174 through its paces while a video display 185 places the handler 159 "inside" the robot as the handler sees through the robot's eye cameras 175 and guides its every movement.

In like manner, a brain wave and/or brain wave pattern-connected individual such as 160 in FIG. 5C could likewise link to the small training robot 174 by connecting lines 184 to lines 171, allowing an even more physically disabled handler 160 to train by putting the training robot 174 through its paces with nothing more than her/his thoughts, a skill that would probably take a good deal of training time to accomplish. In this case as well, a video display 186 would place handler 160 "inside" of proxy robot 174 as the handler trains to manipulate that robot while viewing its surroundings through the robot's eye cameras 175.

All of the training scenarios in FIG. 5 enable a human handler to practice the physical manipulation of a proxy robot, whether virtual or actual, through a process of continuously refining not only movements represented in the muscle (myoelectric) and nervous (neuroelectric) systems of that handler, but also generated within the individual's thoughts, translated into brain waves and brain wave patterns. Such refinement not only takes place within the person of the handler in question, but may also involve a technician changing probe and interface positions to maximize positive outcome. Moreover, in the mind control case represented in FIG. 4, a good deal of machine learning will take place in the brain wave/brain wave pattern interpreter 127, with the assistance of technicians or engineers skilled in the programming and operation of the powerful microcomputer that interpreter represents.

Thus it can be seen that the training scenarios of FIG. 5 encompass not only honing the skill of whichever human handler is undergoing such training, but also of the electronic systems and persons assisting the process through the application of their particular skills.

FIG. 6 illustrates in further detail the means by which a human handler 120, 120a is enabled to control a proxy robot 34 from that handler's brain waves and brain wave patterns, either over a local path 203 or over a distant, remote path 207.

Specifically, contact probes in a skull cap 200 (and 200a in the depicted rear view) are custom-placed to receive appropriate brain waves and brain wave patterns, then amplified in signal amplifiers before being directed in signal cable 215 to a brain wave/brain wave pattern interpreter, signal encoder and wireless transceiver 201, 201a (see FIG. 4), before being transmitted from antenna 202.

Transmission can encompass at least one of three options. In the local path 203 scenario, a local-area signal (on the order of WiFi® or Bluetooth™) is transmitted to another transceiver 211 on proxy robot 34. Follow-me signal commands from the human handler are received by the proxy robot's wireless transceiver 211, which also contains signal decoders and robot motion drivers that operate motion actuators like representative actuators 212. Simultaneously, video signals from the robot's right and left eye cameras 61 and 62, respectively, are sent in the reverse direction over path 203 and received in the head mounted display 63 of human handler 120.

In the second scenario, the handler's transceiver 201, 201a still has local range power, but instead of directly engaging a similar transceiver on a local proxy robot, the signal 204 is transmitted to a local-to-long path relay system consisting of a companion local transceiver 205 that may connect 213 in turn to a long-range transceiver 206 which transmits and receives signals over a long path 207. On the remote (distant proxy robot) end of this two-way signal communication, another long-range transceiver 208 receives signals from and transmits signals to the communication system at the human handler's location. Long-range transceiver 208 may in turn be connected 214 to a short-range, local transceiver 209. The latter transceiver 209 connects over a long-to-local path relay system 210 to a final local transceiver 211 on proxy robot 34.

Alternatively, local-to-long path relay system 204 may consist solely of handler local transceiver 201 in direct communication with long path transceiver 206, and long-to-local path relay system 210 may consist solely of proxy robot local transceiver 211 in direct communication with long path transceiver 209. This alternative connection method, which may eliminate local transceiver 205 and/or local transceiver 208 would depend on the physical layout and infrastructure at each end of the long signal path.

As in the local path scenario above, follow-me signal commands from the human handler are received by the proxy robot's wireless transceiver 211 which also includes signal decoder and robot motion driver means. The resulting decoded follow-me signals are consequently processed by the robot motion drivers and sent to the proxy robot's motion actuators, represented by 212. Concurrently, video signals from the robot's right and left eye cameras 61 and 62, respectively, are sent in the reverse direction over paths 210, 207 and 204 and received in the head mounted display 63 of human handler 120. A third, distant transmission option will be discussed in FIG. 8.

FIG. 7 illustrates myoelectric or neurolelectric means through which a human handler 250 can be enabled to control the movements of a distant proxy robot 34. Such means may include a custom-fitted body suit, subdermal probes, or taped contact pickup points strategically placed around the handler's body.

The human handler 250 is situated inside a motion simulator 251 featuring hydraulic leg elements 252 capable of reproducing various angles of pitch and roll to conform with the terrain or environment the proxy robot 34 is encountering at the remote site. Handler 250 walks, climbs and goes through other movements on an omnidirectional treadmill 253 which measures the handler's orientation (yaw) and sends this information as part of a follow-me signal train to the remote proxy robot. These devices are described at length in the inventor's non-provisional U.S. patent application Ser. No. 14/271,437, now U.S. Pat. No. 9,821,465, entitled "Enhanced Environment Simulator for Proxy Robot Handlers."

Myoelectric and/or neuroelectric pickup points 255 represent symbolically the totality of points on the handler. Each pickup point includes a signal amplifier. All pickup points are connected by wires or cables to a signal processor, encoder and wireless transceiver 260 which first processes follow-me signals from individual pickup points, then encodes the signals into a follow-me signal train before transmitting the follow-me signal train 204 over a local-to-long path relay system.

The local-to-long path relay system consists of a companion local transceiver 205 that may connect 213 in turn to a long-range transceiver 206 which transmits and receives signals over a long path 207. On the remote (distant proxy robot) end of this two-way signal communication, another long-range transceiver 208 receives signals from and transmits signals to the communication system at the human handler's location. Long-range transceiver 208 may in turn be connected 214 to a short-range, local transceiver 209. The latter transceiver 209 connects over a long-to-local path relay system 210 to a final local transceiver 211 on the proxy robot 34.

Alternatively, local-to-long path relay system 204 may consist solely of handler local transceiver 201 in direct communication with long path transceiver 206, and long-to-local path relay system 210 may consist solely of proxy robot local transceiver 211 in direct communication with long path transceiver 209. This alternative connection method, which may eliminate local transceiver 205 and/or local transceiver 208 would depend on the physical layout and infrastructure at each end of the long signal path.

In either case, follow-me signal commands from the human handler 250 are received by the proxy robot's wireless transceiver 211 which also includes signal decoder and robot motion driver means. The resulting decoded follow-me signals are consequently processed by the robot motion drivers and sent to the proxy robot's motion actuators, represented by 212. Concurrently, video signals from the robot's right and left eye cameras 61 and 62, respectively, are sent in the reverse direction over paths 210, 207 and 204 and received in the head mounted display 63 of human handler 120. Right and left eye camera video may also be sent to an optional wrap-around video display screen 254 in the motion simulator 251.

Figure 8:
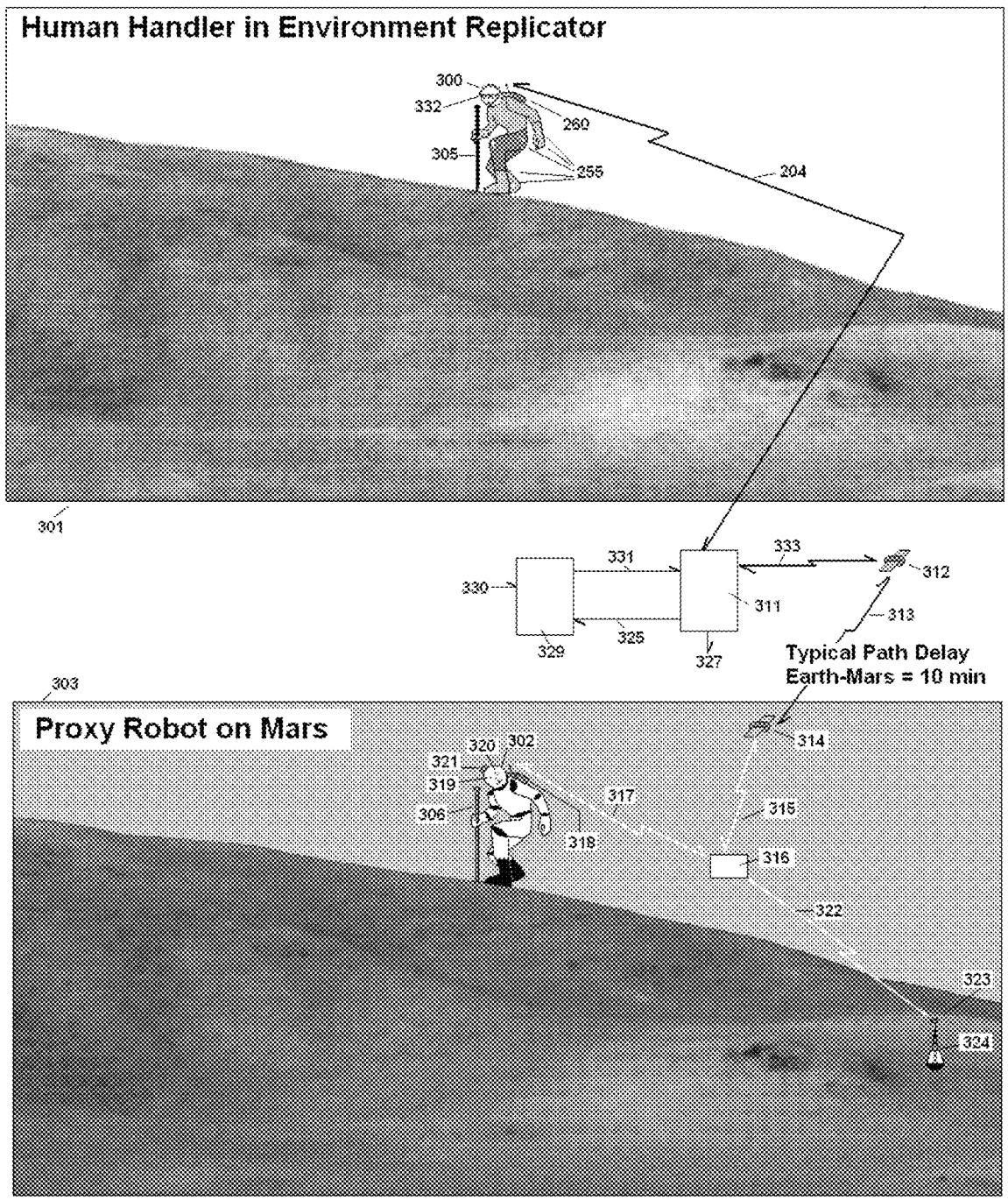
FIG. 8 illustrates control of a proxy robot on Mars by a human handler on Earth in accordance with embodiments of the invention.

FIG. 8 depicts a scenario requiring a long two-way communication path between a human handler 300 in an environment replicator on Earth and a proxy robot 302 on a distant planet 303 such as Mars. As in FIG. 7 above, the handler is an able-bodied human in a body suit or otherwise connected to a series of contact points represented by 255. Each contact point picks up myoelectric and/or neuroelectric signals which are amplified on location by a signal amplifier. All pickup points are connected by wires or cables to a signal processor, encoder and wireless transceiver 260 which first processes follow-me signals from individual pickup points, then encodes the signals into a follow-me signal train before transmitting the follow-me signal train 204 over a local transmission path to a series of electronic devices (below).

The proxy robot 302 is carrying a tool of some sort 306, and handler 300 similarly carries a replica tool 305 so as to be able to guide the proxy's use of that tool.

The follow-me signals are decoded by an Earth-to-satellite transceiver 311 in close proximity to environmental replicator 301, and then transmitted by transceiver 311 over path 333 to a satellite 312 orbiting Earth. This satellite is in communication (whether directly or through a satellite network) with another satellite 314 orbiting Mars. Satellite 314 receives the follow-me data signals and transmits them in turn 315 to a transceiver 316 on the surface of Mars, which further relays 317 the follow-me signals originating with the human handler 300 on Earth to a local transceiver 318 on the proxy robot 302, which also contains the electronic systems needed to decode those signals and turn them into movement commands for motion actuators 310 in appropriate locations on the proxy robot.

Like the proxy robots in preceding figures, proxy 302 has video cameras 319 and 320 in its right and left eye sockets, as well as a 360-degree, long-range video camera 321 capable of accurately seeing where the robot might be in ten or twenty minutes or even greater time. This long-range view all around the proxy robot is a major component of the rendering of a accurate approximated real-time video stream (below). Video data from all three cameras on the proxy robot is transmitted by proxy transceiver 318 back to transceiver 316.

Concurrently, video and location data 323 from one or more observation devices such as buoy camera 324 is likewise transmitted by that buoy camera to transceiver 316, which also includes video and data encoder circuitry which aggregates all the outgoing signals for transmission to orbiting Mars satellite 314. Environment replicator and buoy camera concepts are disclosed at length in inventor's non-provisional application Ser. No. 14/594,128, now U.S. Pat. No. 9,823,070 entitled "Remote Reconnaissance for Space Exploration."

It should be pointed out that there is another way to achieve the same objectives which does not require transceiver 316. In this alternative, the proxy robot's transceiver 318 takes on all the functions of transceiver 316. Thus, in addition to the functions already listed for the proxy transceiver 318, it would also communicate directly with Mars-orbiting satellite 314 as well as with mission site transceivers such as the one in the camera and communication head 323 of buoy camera 324.

In either case, Mars satellite 314 will relay 313 the signals from proxy robot 302 and camera/locator means such as buoy camera 324 back to Earth-orbiting satellite 312, which in turn transmits them 333 to transceiver 311 and its decoder circuitry. From this decoder, a stream of direct but path-delayed video from all Mars cameras as well as location and other terrain data is made available 327 for the analysis of mission control personnel.

The Mars-originating video and data is also channeled 325 to a powerful terrain analysis computer 329. Combining this incoming video and data with previously-stored video, photographs and other data 330 pertinent to the mission site gives computer 329 the ability to rapidly generate an approximated real time (ART) video stream 331 which is sent 204 from local transceiver 311 to a head-mounted display 332 on the person of human handler 300.

The ART video stream 331 in the handler's head-mounted display 332 is virtual rather than actual, a computer simulation based on the most accurate available views and information about the terrain where the proxy robot is operating. This is necessitated by the simple fact that long-distance missions such as those to Mars entail a significant path delay. Based mainly on the time it takes radio signals to go to or from Mars considering the then-current distance between the two planets and the speed of light, the path delay can vary from a minimum of approximately 3 minutes to a maximum of over 22 minutes each way. Operating in this "future time frame" allows the human handler 300 to see what the robot will see at the exact moment the handler's follow-me signals arrive to direct that robot's next moves. ART video generation and related concepts are disclosed in the inventor's non-provisional application Ser. No. 13/970, 910, now U.S. Pat. No. 9,623,561, entitled "Real Time Approximation for Robotic Space Exploration."

Figure 9:
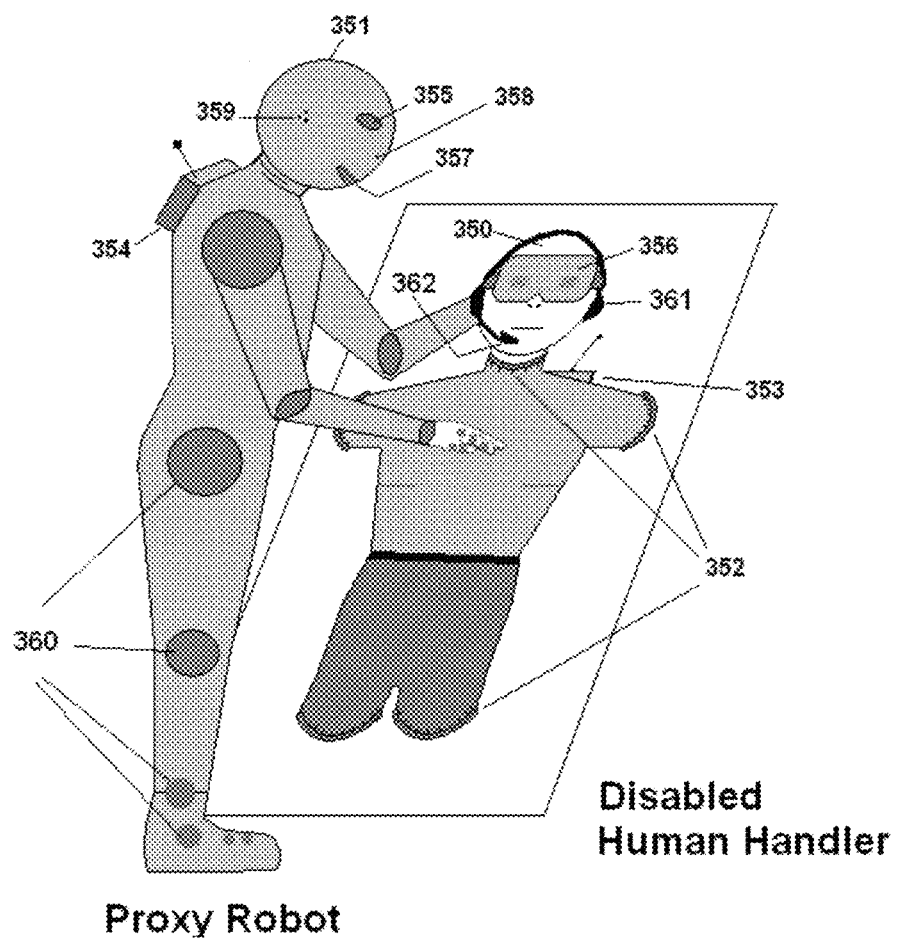
FIG. 9 is an exemplary illustration of a disabled human handler with a proxy robot caregiver in accordance with embodiments of the invention.

FIG. 9 shows an earthly use for the current invention, illustrating means through which a physically disabled human can cause a proxy robot to be her own caregiver. In the drawing, a human handler 350 has lost all four limbs, but this is only one representation of a disabled person who may instead be paralyzed or through accident, disease or genetic reasons have lost control of certain body motor functions. In the case at hand, amputee handler 350 is able to send follow-me commands to proxy robot 351 by means of myoelectric and/or neuroelectric signals originating at the neck and at each stump 352.

In brief, the myoelectric and neuroelectric signals are amplified on-location by signal amplifiers and sent to processor-encoder-transceivers 353 for transmission to a transceiver 354 on the proxy robot which also includes circuitry to decode the follow-me signals and send them to motion actuators 360 (FIG. 9 shows a representative motion actuator sampling) which cause the robot to move in accordance with the will and instructions of the human handler. The power level of transceivers 353 and 354 should at least be sufficient to permit clear communication in the living quarters and neighborhood of the handler in question, and may as well be sufficiently powerful to allow the handler to send the proxy to do tasks like shopping.

Such a task as shopping would require the proxy robot to have not only eye cameras (below), but also microphone "ears" 359 (only right ear shown) and a speaker "mouth" 357. Such appendages on the proxy robot 351 permit the human handler 350 to wear a headset, complete with earphones 361 to hear what the robot hears and microphone 362 into which the handler can speak so that her or his voice may be relayed to the mouth opening of the proxy robot: "Sir, can you direct me to the deli section?"

In addition to "ears" and "mouth", the proxy robot has two camera "eyes" (only right eye 355 is visible in the drawing) which relay everything the robot sees back to a head mounted display 356 worn by the handler. So in the illustration of FIG. 9, the disabled handler is quite literally "inside" of the proxy robot, seeing her (handler's) own body and extending care with robotic arms and hands. Additionally, a robotic "nose" 358 may serve to identify smoke, toxic gas and other airborne particles that might require warning on the robot's part and possible evasive action from the handler.

All of these signals—video from the robot's camera "eyes", smoke and gas analysis data from its "nose" and sounds turned into audio from its "ears"—are sent from proxy robot 351 back to human handler 350 over the path between the robot's transceiver 354 and the transceiver 353 of the handler. Additional feedback may include haptic sensations such as heat or cold; roughness or smoothness; and pressure, including pushing, pulling and weighing (heft). Certain feedback signals from proxy robot 351 may be displayed on a monitor or translated to sound for human handler 350 and/or sent to a monitoring center.

FIG. 10 illustrates how various biocontrol methods may be used concurrently. In FIG. 10A, a human handler 400 whose right leg is missing is enabled to control a proxy robot 34 by means of myoelectric and/or neuroelectric signals from right leg stump 82; myoelectric and/or neuroelectric signals from contact points 404 (representative points shown) strategically located all over the handler's body; and brain wave signals and patterns from a customized skull cap 401 which also contains amplifiers for each signal.

In the case of stump 82, a cap with surface or subdermal contact points 83 connects 84 to signal amplifiers 85, one for each contact. The amplified signals 403 are routed 403a to transceiver 405, 405a which includes a processor for each myoelectric or neuroelectric signal. Meanwhile, an additional brain wave/wave pattern interpreter circuit in handler transceiver 405 turns the amplified signals from skull cap 401, 401a into signals compatible with those processed from the body and leg stump of the handler. Transceiver 405, 405a also includes an encoder to aggregate and encode the totally of signals as follow-me commands for transmission over local path 406 to a transceiver 211 on the proxy robot.

On the proxy robot 34 side, transceiver 211 also contains a signal decoder and a set of robot motion drivers suitable to cause appropriate motion actuators 407 (representative sample) to activate and make the robot move in accordance with the follow-me commands from handler 400.

Concurrently, video signals from the robot's right and left eye cameras 61 and 62, respectively, are sent in the reverse direction over path 406 and received in the head mounted display 63 of human handler 400. As in FIG. 9 above, additional feedback may include haptic sensations such as heat or cold; roughness or smoothness; and pressure, including pushing, pulling and weighing (heft). Certain feedback signals from proxy robot 34 may be displayed on a monitor or translated to sound for human handler 63 and/or sent to a monitoring center (not shown).

FIG. 10B depicts the human handler and proxy robot of FIG. 10A, but in this drawing proxy robot 34 is very remote from handler 400, for example, undertaking a proxy robotic mission on Mars or some other location in space. Although many types of nervous system pickup means are depicted, FIGS. 10A and 10B are exemplary in nature, illustrating that any combination of myoelectric, neuroelectric and brain wave pickup may be utilized—in whole, in part, or in combination with other motion capture means—in the remote control of a proxy robotic device by a human handler.

On handler 400 in FIG. 10B a plurality of electrical signal pickup points are shown, including points 83 on the stub of the handler's left leg, points 404 in hinge and muscle areas throughout the handler's body, and brain wave points on the inside of skull cap 401. Contacting each of these signal pickup points is an electrode 410 which may be secured against the skin by tape or other means, held in position by a body suit, or implanted subdermally in ways ranging from a small acupuncture-like needle to surgical implantation.

Each electrode 410 is connected to an individual signal amplifier 411 placed in proximity to the pickup signal point to maximize the signal over ambient noise. Each signal amplifier 411 is connected in turn 412 to its own signal processor 413 which is customized to render each processed signal 414 in conformity with the level, impedance and other input requirements of A/D converter 415. A plurality of A/D converters 415 convert all of the amplified and processed signals from the body of handler 400 to digital signals 416. Through individual input ports, the parallel digital signals 416 enter a parallel-to-serial converter 417 that aggregates all the parallel digital signals and converts them into a single digital stream 418.

Digital stream 418 is directed to a follow-me computer 419 that encodes stream 418 into a follow-me data stream 420 suitable for transmission by a transmitter 421 and antenna 422 over a long path 423 that may include retransmission by satellites and other relay means (not shown) to an antenna 424 and receiver 425 at the remote location in space. The received follow-me data stream 426 is directed into a deaggregator 427 which decodes the stream into individual signals 428 by converting the serial follow-me data stream 426 back into its original parallel components 428 reflecting individual signals 416 on the human handler side, with each signal 416, 428 corresponding to an individual pickup point on the body of handler 400. Each parallel individual signal component 428 is directed to its own follow-me data translator 429 which translates that follow-me signal 428 into a motion actuator drive signal 430 appropriate to address an individual motor, hinge or other motion actuator in proxy robot 34 at the remote location in space and thereby control—in concert with all the other translated follow-me signals 430—the remote proxy robot's every move.

The various features of the invention described herein can be implemented in different systems without departing from the invention. It should be noted that the foregoing aspects of the disclosure are merely examples and are not to be construed as limiting the invention. The description of the aspects of the present disclosure is intended to be illustrative, and not to limit the scope of any claims. As such, the present teachings can be readily applied to other types of apparatus and many alternatives, modifications, and variations will be apparent to those skilled in the art.

I claim:

1. A method for training a human handler of a proxy robot surrogate (handler) to control the movements of a training proxy robot by utilizing electrical signals from the handler's nervous system, comprising:
    scanning a body of the handler to identify optimal electrical signal pickup points;
    connecting electrodes to the electrical signal pickup points;
    amplifying electrical signals from each signal pickup point by a signal amplifier;
    processing the amplified electrical signals from each signal pickup point;
    aggregating the processed electrical signals originating from each of the signal pickup points into a bundle of handler output lines;
    selectively connecting the bundle of handler output lines and their component electrical signals to a set of robotic motion drivers,
    wherein each component electrical signal corresponds to an electrical signal from a particular pickup point on the body of the handler;
    processing each component electrical signal by a driver configured for an individual motion-producing element (motion actuator) in the training proxy robot;
    addressing by the component electrical signals each motion actuator in a motor system of the training proxy robot,
    wherein the motion actuators cause the training proxy robot to emulate movements of the handler; and
    providing the handler with a continuous view of the training proxy robot's surroundings and movements from video eye cameras in the training proxy robot.

2. The method of claim 1, wherein the electrical signals from the nervous system of the handler comprise myoelectric signals.

3. The method of claim 1, wherein the electrical signals from the nervous system of the handler comprise neuroelectric signals.

4. The method of claim 1, wherein the electrical signals from the nervous system of the handler comprise signals from the brain of the handler.

5. The method of claim 1, wherein processing each component electrical signal comprises translating each component electrical signal from the handler into operating code for the training proxy robot.

6. The method of claim 1, wherein aggregating the processed electrical signals comprises parallel-to-serial conversion of the signals.

7. A method for training a disabled person (user) to control the movements of a training proxy robot surrogate by utilizing electrical signals from the user's nervous system, comprising:
    scanning a body of the user to identify optimal electrical signal pickup points;
    connecting electrodes to the electrical signal pickup points;
    amplifying electrical signals from each signal pickup point by a signal amplifier;
    processing the amplified electrical signals from each signal pickup point;
    aggregating the processed electrical signals originating from each of the signal pickup points into a bundle of user output lines;
    encoding the aggregated processed electrical signals for transmission over a path to the proxy robot surrogate;
    receiving the aggregated processed electrical signals at the location of the proxy robot surrogate;
    decoding the aggregated processed electrical signals into their original component electrical signals,
    wherein each component electrical signal corresponds to an electrical signal from a particular pickup point on the body of the user;
    processing each component electrical signal by a driver configured for an individual motion-producing element (motion actuator) in the training proxy robot surrogate;
    addressing by the component electrical signals each motion actuator in a motor system of the training proxy robot surrogate,
    wherein the motion actuators cause the training proxy robot surrogate to emulate movements of the user; and
    providing at least one user display device with continuous feedback in the form of streaming video of the training proxy robot's surroundings and movements from eye cameras in the training proxy robot surrogate.

8. The method of claim 7, wherein training the disabled user to control the movements of a training robot comprises training the user to remotely control the movements of a service robot by utilizing signals from the user's nervous system.

9. The method of claim 7, wherein processing each component electrical signal comprises translating each component electrical signal into operating code to address corresponding motion actuators in the training proxy robot surrogate.

10. A system for training the human handler of a proxy robot surrogate (handler) to control the movements of a training proxy robot by utilizing electrical signals picked up from the handler's nervous system, comprising:
    a plurality of electrodes optimally placed in contact with electrical signal pickup points on the body of the handler,
    wherein each individual electrode is in contact with one signal pickup point;
    a plurality of amplifiers placed in proximity to and connected to the plurality of electrodes,
    wherein each amplifier amplifies an electrical signal received from an individual electrode;
    a plurality of electrical signal processors to render each amplified electrical signal to conform with the requirements of an analog-to-digital (A-D) converter;
    a plurality of A-D converters to convert the electrical signal associated with each signal processor from analog to digital, wherein each of the plurality of A-D converters produces an individual digital signal representative of one of the electrical signals from the plurality of electrodes;
a bundle of output lines for transporting each of the individual digital signals;
an encoder to aggregate the individual digital signals into a single digital signal stream,
wherein the encoder comprises a parallel-to-serial converter;
a decoder at the site of the training proxy robot to deaggregate the digital signal stream into its individual signal components;
a plurality of robotic motion drivers to selectively receive the plurality of individual signal components,
wherein each individual signal component is processed by its driver to address a particular robotic motion actuator in the training proxy robot;
a plurality of robotic motion actuators in the training proxy robot to receive the digital signals from their respective drivers,
wherein the robotic motion actuators cause the training proxy robot to emulate movements of the handler; and
video eye cameras in the training proxy robot to provide the handler with continuous feedback views of the training proxy robot's surroundings and movements.

11. The system of claim 10, wherein the deaggregator translates handler movements into operating code for the training proxy robot.

12. The system of claim 10, wherein the deaggregator comprises a serial-to-parallel converter.

13. The system of claim 10, wherein the robotic motion actuators comprise motors.

14. The system of claim 10, wherein the robotic motion actuators comprise solenoids.

15. The system of claim 10, wherein the robotic motion actuators comprise hinges.

16. The system of claim 10, wherein the digital signals addressed to the robotic motion actuators are translated into analog signals.

17. The system of claim 10, wherein the robotic motion actuators comprise elastic materials.

18. The system of claim 10, wherein the robotic motion actuators comprise artificial muscles.

19. The system of claim 10, wherein the robotic motion actuators comprise hydraulic mechanisms.

20. The system of claim 10, wherein training the handler to control the movements of a training proxy robot comprises training the handler to control the movements of a proxy robot surrogate at a remote location.

* * * * *